United States Patent [19]

Sanchez et al.

[11] Patent Number: 5,308,874
[45] Date of Patent: May 3, 1994

[54] AIRBORNE PROTECTANTS AGAINST OXIDATIVE TISSUE DAMAGE

[75] Inventors: Robert A. Sanchez, Carlsbad; Sheldon S. Hendler, La Jolla, both of Calif.

[73] Assignee: Vyrex Corporation, La Jolla, Calif.

[21] Appl. No.: 905,585

[22] Filed: Jun. 26, 1992

[51] Int. Cl.$^5$ .............................................. A61K 31/05
[52] U.S. Cl. .................................. 514/731; 514/957; 514/958
[58] Field of Search ............... 514/957, 958, 717, 718, 514/731; 424/197.1, 10

[56] References Cited

U.S. PATENT DOCUMENTS

| | | | |
|---|---|---|---|
| 214,240 | 4/1879 | Compton | 424/197.1 |
| 649,826 | 5/1900 | Eldred | 514/731 |
| 1,922,488 | 8/1933 | Mengering | 424/195.1 |
| 3,339,558 | 9/1967 | Waterbury | 514/725 |
| 3,632,782 | 1/1972 | Alburn et al. | 514/731 |
| 4,084,006 | 4/1978 | Leach | 514/731 |
| 4,350,707 | 9/1982 | Keith et al. | 424/346 |
| 4,414,217 | 11/1983 | Moore | 424/263 |
| 4,663,315 | 5/1987 | Hasegawa et al. | 514/957 |
| 4,695,590 | 9/1987 | Lippman | 514/724 |
| 4,720,564 | 9/1988 | Kakimoto et al. | 556/83 |
| 4,778,673 | 10/1988 | Vernizzi et al. | 514/957 |
| 4,857,325 | 8/1989 | Albeck et al. | 424/195 |
| 4,976,960 | 12/1990 | Grossman et al. | 424/195 |
| 5,017,614 | 5/1991 | Pariza et al. | 514/558 |
| 5,071,873 | 12/1991 | Kakimoto et al. | 514/492 |
| 5,082,661 | 1/1992 | Melnik et al. | 514/922 |

FOREIGN PATENT DOCUMENTS 459942  1/1937  United Kingdom .

*Primary Examiner*—Frederick E. Waddell
*Assistant Examiner*—Raymond J. Henley, III
*Attorney, Agent, or Firm*—Townsend and Townsend Khourie and Crew

[57] ABSTRACT

Disclosed are methods for preventing free radical-induced oxidative damage and inflammatory response in biological tissue. The methods comprise exposing biological tissue to vapor-phase, phenolic antioxidants such as vaporized 2,6-diisopropylphenol.

7 Claims, No Drawings

AIRBORNE PROTECTANTS AGAINST OXIDATIVE TISSUE DAMAGE

FIELD OF THE INVENTION

The present invention relates to methods for preventing oxidative damage to biological tissue. In particular, the methods comprise exposing biological tissue to a phenolic antioxidant compound in its vapor form.

BACKGROUND OF THE INVENTION

Among the most common causes of damage to biological tissue are oxidative processes that result in the production of free radicals. These highly reactive species frequently cause unwanted reactions which can damage biological tissues. In addition, free radicals can initiate chain reactions that result in the continued formation of new free radicals. Such chain reactions can damage many constituent molecules that comprise biological tissue before the reactions are ultimately terminated.

Free radicals can be formed by any one, or a combination, of a large number of oxidizing agents, oxidation-inducing agents and certain microbial agents including certain viruses. Examples of well-known oxidizing agents which promote the production of free radicals include the following: ozone, oxygen, halogens, hypochlorite (bleach), nitrogen oxides, hydrogen peroxide, ionizing radiation, combustion products, and ultraviolet radiation. Examples of oxidation-inducing agents include the chemotherapeutic agents doxorubicin (Adriamycin®) and bleomycin (Bleonoxane®). Examples of some viruses that appear to produce tissue damage by causing increased oxidizing activity include HIV (human immunodeficiency virus, or AIDS virus) and influenza virus. Although most oxidizing agents are naturally occurring substances, many of them are produced in large quantities from artificial sources such as internal combustion engines, cigarettes, electrical equipment, arc discharge sources, high energy lamps, water treatment procedures, and commercial manufacturing and processing operations.

The biological damage that is produced by the aforementioned oxidizing agents is primarily due to their involvement in the production of free radicals. Often, free radicals cause unwanted biological damage by creating structural damage to lipids, nucleic acids, protein, and many other biomolecules. The following are representative examples of free radical-induced biological damage.

Humans and most living organisms require some exposure to sunlight for optimum health. However, exposure to the shorter wavelength components of sunlight (ultraviolet e.g., 320 nm or shorter) can cause topical tissue damage such as erythema (sunburn), premature aging of the skin (e.g., drying, wrinkling, loss of elasticity, abnormal pigmentation), cancer and activation of viruses such as herpes as well as immune suppression. It is believed that much of the damage caused by sunlight is the result of chain reactions which originate when the ultraviolet light promotes the production within the tissue surface of free radicals such as superoxide and hydroxyl. Similar processes of free radical tissue damage are caused by exposure to other forms of energetic radiation such as radioactivity, X-rays, gamma rays and the like.

Smoking is known to be a major cause of lung cancer, emphysema, and other respiratory tract diseases, as well as cardiovascular diseases. Even non-smokers who are exposed to tobacco smoke (i.e., "second hand smoke") are at a higher risk for these disorders. Tobacco smoke, as well as byproducts of other combustion processes (e.g., internal combustion engines, heating and cooking with fuels, natural fires) are known to contain free radical species which are thought to be major contributors to tissue damage.

Several other forms of respiratory tract damage are thought to be linked to free radical oxidation. These other forms include respiratory distress syndrome, pulmonary vasoconstriction, influenza, pneumonia, asthma, damage caused by ischemia reperfusion, and damage resulting from auxiliary breathing systems or respirator therapies that involve the use of supplemental oxygen and/or increased gas pressure.

A very common result of respiratory tract damage and of virtually all forms of oxidative tissue damage is inflammation. In the respiratory tract, inflammation, whether caused by chemical agents, radiation, microbes or viruses, contributes to difficulty in breathing and to impairment of oxygen transport into the blood.

Antioxidants are chemical compounds that inhibit free radical oxidation by neutralizing free radicals. Biological systems generally contain internal mechanisms to protect against oxidative free radical damage. Organisms including humans have at least two different classes of antioxidants useful in preventing oxidative damage. One class, known as antioxidant enzymes, is normally produced by the body's own cells, and serves to neutralize various types of free radicals throughout the body. For example, superoxide dismutase (SOD) is a natural antioxidant enzyme that converts the superoxide radical into a less harmful species. Additionally, glutathione peroxidases and catalase remove excess hydrogen peroxide—a compound that is harmful to cells and can generate free radicals. A second class of antioxidants present in biological organisms includes certain nutrients. For example, vitamins E (tocopherol), C (ascorbate), and beta-carotene are all known to be antioxidants and free radical scavengers.

Additionally, phenolic antioxidants, both natural and synthetic, are commonly used to counteract and/or prevent free radical-induced oxidative damage. Butylated hydroxytoluene (BHT) and butylated hydroxyanisole (BHA) are examples of synthetic antioxidants that are added to pastries, oils, and other foods to retard rancidity. Probucol, another synthetic antioxidant, is effective in animal, and humans against lipid oxidation and atherosclerosis. Vitamin E, mentioned above, is an example of a naturally occurring material used to counteract or prevent oxidative damage.

Antioxidants for human use are usually provided orally as a solid (e.g. tablet), liquid, or liquid solution. For example, beta-carotene and vitamins C and E are commonly taken as solids (tablets, capsules) or as solutions. The drug Lorelco (probucol) is typically taken as a tablet. (Physicians Desk Reference, 43rd edition, 1989, page 1415). Occasionally, an antioxidant may be administered via inhalation, in the form of an aerosol. See, for example, Z. Borok et al., "Effect of glutathione aerosol on oxidant-antioxidant imbalance in idiopathic pulmonary fibrosis" *Lancet* 338(8761), 215-216 (1991), and R. Buhl et al., "Augmentation of glutathione in the fluid lining of the epithelium of the lower respiratory tract by directly administering glutathione aerosol" *Proceedings of the National Academy of Sciences* 87(11), 4063-4067

(1990), both of which are incorporated herein by references for all purposes. Fine droplets, however, are difficult to uniformly produce and deliver to relatively inaccessible sites. For example, spray droplets delivered via inhalation tend to accumulate in the upper respiratory tract, without penetrating into the inner reaches of the lung.

Thus, it can be seen that there is a need for a penetrating, easy to deliver form of antioxidant. This type of antioxidant can have very important medical and environmental health benefits.

SUMMARY OF THE INVENTION

It has been discovered that certain antioxidants (particularly phenolic, radical-inhibiting antioxidants) considered to be slightly volatile or substantially nonvolatile under ordinary conditions of temperature and pressure, are, in fact, sufficiently volatile and of sufficiently high antioxidant potency that they are capable of providing gasborne protection against oxidative stress and oxidative damage. The present invention provides methods and apparatus for ameliorating oxidative stress and oxidative damage to biological tissue by exposing that tissue to vapor-phase, phenolic antioxidants.

Efforts have been made to find suitable methods for preventing oxidative damage. However, of the methods known to date, none involve the gasborne delivery of antioxidant compounds to biological tissue experiencing oxidative stress or oxidative damage. Exposing biological tissue to vapor-phase, phenolic antioxidant compounds has unique advantages. In contrast to particulate agents such as aerosols, sprays, powders and creams, vapor-phase antioxidants will not settle out of air, and thus, are more permeant in porous and finely channeled structures. These features are particularly advantageous for the delivery of such antioxidants to the respiratory system, since a gas has far more penetrating and uniform access to the intricate recesses of the pulmonary tissue.

The methods and apparatus of the present invention can take the form of a variety of embodiments. In one embodiment, for example, an antioxidant is incorporated into a tobacco product (e.g., cigarettes, pipes, and cigars) which is vaporized while smoking and subsequently inhaled into the smoker's lungs where it can protect against the toxic oxidative effects of tobacco smoke.

In another embodiment, the method comprises placing the biological tissue in an atmospheric chamber, tent or other environment or enclosure that has been filled with an antioxidant compound. Humans, animals, plants, and various foods can be placed in such environments, and thus, directly exposed to antioxidant compounds. In some embodiments, exposure to the biological tissue is provided through evaporation of the antioxidant, or of the antioxidant mixed with a pharmaceutically acceptable carrier, compound or adsorbent.

In a further embodiment, the vapor form of the antioxidant is one component of a gas mixture contained in a therapeutic breathing device, such as a respirator, lung machine or hyperbaric device. Additionally, gasphase antioxidants may be added to the breathing apparatuses used by scuba divers, firemen and other workers exposed to hazardous working environments. In these embodiments, the antioxidant can be provided in a standard pressurized gas tank.

Other advantages, features and embodiments of the present invention will become apparent from the detailed description which follows.

DETAILED DESCRIPTION OF THE INVENTION AND PREFERRED EMBODIMENTS

This invention relates to methods for preventing oxidative damage to biological tissue by exposure to vapor-phase antioxidant compounds. As used herein, the term antioxidant refers to compounds that can neutralize the biologically damaging effects caused by free radicals, especially free radicals formed or initiated by an oxidizing agent. Preferred antioxidants will have a sufficiently high vapor pressure that a "significant amount" of the antioxidant is present in the gas phase when at equilibrium under mild conditions (e.g., at or near ambient temperatures and pressures on the earth's surface). A "significant amount" of anitoxidant is that quantity of antioxidant that can effect some protection of biological tissue from damage by free radicals. Preferably, the antioxidant compounds will be of the phenolic type.

Preferred phenolic antioxidant compounds in accordance with the present invention are those having the following structural formula:

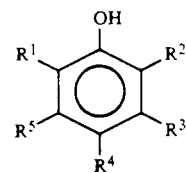

In the above formula, $R^1$ and $R^2$ are independently selected and may be functional groups including, but not limited to H and lower alkyls of 1 to 4 carbon atoms. $R^3$, $R^4$ and $R^5$ are independently selected and may be functional groups including, but not limited to H, lower alkyls of 1 to 6 carbon atoms, lower alkoxys of 1 to 4 carbon atoms, and lower alkyls of 1 to 4 carbon atoms in which one or more of the carbon atoms is replaced with a heteroatom, such that any remaining valences are filled with H, and with the proviso that the total number of carbons and heteroatoms in groups $R^3$, $R^4$ and $R^5$ does not exceed 5.

The term "independently selected" is used herein to indicate that two or more of the R groups may be identical or each R group may be different. Further, two of these groups may together form a ring. The term "alkyl" is used herein to refer to saturated hydrocarbon groups that can be either straight-chain or branched-chain. The term "alkoxy" is used herein to refer to alkyl radicals that are attached to the phenolic ring through the oxygen (e.g., a methoxy group). The term "heteroatom" is used herein to refer to oxygen, sulfur and nitrogen atoms. Exemplary compounds include 2,6-diisopropyl-4-methylphenol, 2,4,6-triisopropylphenol, 2, 6 diisopropyl-4,5-methylenedioxyphenol, 2-methyl-6-tert-butyl-4-methylthiophenol, and 2,6-diisopropyl-3,4,5-trimethylphenol.

Further preferred phenolic antioxidant compounds in accordance with the present invention are those having the following structural formula:

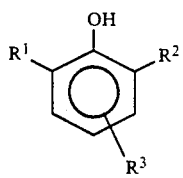

In the above formula, $R^1$ and $R^2$ are independently selected and may be functional groups including, but not limited to H and lower alkyls. $R^3$ is independently selected and may be a functional group including, but not limited to H, lower alkyls and lower alkoxys. In the above formula, $R^3$ is denoted as a floating group. The term "floating group" is used herein to refer to the fact that $R^3$ may be placed either at position 3, 4, or 5 of the benzene ring.

Within the scope of the present invention, certain antioxidant compounds are preferred, namely those in which $R^1$ is H, $CH(CH_3)_2$, or $C(CH_3)_3$; $R^2$ is H, $CH(CH_3)_2$, or $C(CH_3)_3$; and $R^3$ is H, $CH_3$, or $OCH_3$. In particular, the following antioxidants are preferred: 2,6-di-tert-butylphenol, 2,6-di-tert-butyl-4-methylphenol (BHT), and 2(3)-tert-butyl-4-methoxyphenol (BHA) 2,6-diisopropyl-4-methylphenol, 2,4,6-triisopropylphenol, 2,6 diisopropyl-4,5-methylenedioxyphenol, 2-methyl-6-tert-butyl-4-methylthiophenol, and 2,6-diisopropyl-3,4,5-trimethylphenol. A specific preferred compound in the present invention is the antioxidant compound 2,6-di-isopropylphenol.

Many preferred compounds of the present invention will have a relatively high vapor pressure at room temperatures. Suitable compounds will typically have a boiling point (at 1 atmosphere) of less than about 400° C. For example, the following useful compounds have the noted boiling points:

| Compound | b.p. °C. | reference |
| --- | --- | --- |
| 2,6-diisopropylphenol | 256° | a |
| 2,6-di-tert-butylphenol | 253° | a |
| 2,6-di-tert-butyl-4-methylphenol (BHT) | 265° | b |
| 2(3)-tert-butyl-4-methoxyphenol (BHA) | 270° | b |
| 2,4,6-tri-tert-butylphenol | 277° | a |
| tert-butylhydroquinone | 295° | c | a. Aldrich Chemical Company, Milwaukee, Wisconsin. 1990-1991 Catalog.
b. Merck Index, Merck & Co., Inc., Rahway, New Jersey. 10th Edition, 1983.
c. UOP, Des Plaines, Illinois. Brochure. "Sustane ® food-grade antioxidants", 1991.

References "a", "b", and "c" are incorporated by reference herein for all purposes.

In a preferred method of the present invention, a safe and effective amount of an antioxidant compound is incorporated into a tobacco product, vaporized upon smoking, and inhaled into the lungs and respiratory tracts of the smoker. Such tobacco products include, but are not limited to cigarettes, pipes and cigars. The antioxidant compounds may be incorporated into either the filter or the body of such tobacco products. In this method, the antioxidants 2,6-di-isopropylphenol, 2,6-di-tertbutylphenol and 2(3)-tert-butyl-4-methoxyphenol (BHA) are particularly useful. When added to the filter of a cigarette, these compounds effectively inhibit free radical-induced oxidative processes.

In another preferred method of the present invention, various forms of biological tissue may be placed in environmental chambers, tents or enclosures that contain safe and effective amounts of volatile antioxidant compounds. Exposing biological tissue to antioxidants in this manner effectively protects against free radical-induced oxidative damage (and inflammation if the tissue is part of a mammal or other higher organism). Humans, animals, plants and various foods may be placed in these chambers and exposed to antioxidant compounds. For example, when a thin strip of freshly sliced thin beef is placed in a chamber containing an antioxidant compound, the oxidative damage which would normally result during exposure to incandescent illumination and bright sunlight is inhibited. Similar results are found when linseed oil is placed in an environmental chamber containing an antioxidant compound. 2,6-diisopropylphenol has been found to be particularly effective at inhibiting this type of oxidative damage.

In a further preferred method of the present invention, a phenolic antioxidant is one element of a gas mixture delivered with a therapeutic breathing device (e.g., respirators or lung machines). Alternatively, antioxidant compounds may be added to a filter or some other delivery reservoir in these devices such that as air is drawn through the device, the antioxidants are vaporized and subsequently inhaled. When the gas is inhaled through the use of a breathing apparatus, the antioxidant compound is brought into the respiratory tract of a mammal where it can effectively prevent oxidative damage. Often oxidative damage can result from auxiliary breathing devices or respirator therapies that involve the use of supplemental oxygen and/or increased gas pressure (e.g. hyperbaric devices). However, when antioxidant compounds are incorporated into the gases used in these breathing apparatuses, the oxidative damage that would normally result is minimized and often totally prevented. Phenolic antioxidants may similarly be used in the breathing devices used by scuba divers, firemen and other workers who are exposed to hyperbaric pressure and/or hazardous working conditions where strong oxidizing agents are present.

Another preferred method of the present invention includes steps of (1) vaporizing a relatively volatile antioxidant compound, and (2) exposing biological tissue to this vaporized, volatile antioxidant. These compounds can be added to a vaporizer (i.e., a device used to vaporize medicines and other compounds) and upon vaporization, they are inhaled into the respiratory tract where they effectively inhibit oxidative processes. Additionally, they can be added to a hand-held inhalator (i.e., a device that produces a vapor to medicate by inspiration) and upon inhalation, the antioxidant is delivered to the lungs where it inhibits free radical-induced oxidative processes therein.

Additionally, through the use of devices such as vaporizers and inhalators, biological tissue can be exposed to compositions which contain a volatile antioxidant and which further contain a pharmaceutically acceptable carrier, compound, or adsorbent. Such materials might take the form of inert gases, liquids or solids which assist in the vaporization and delivery of the antioxidant. In some embodiments, the antioxidant may be provided as a mist of fine droplets that are at least partially vaporized in a flow stream of inert gas or air.

The following examples are offered for illustrative purposes, and are intended neither to limit nor define the invention in any manner.

EXAMPLE I

The following experiment is based on the use of low density lipoprotein (LDL) as an oxidizable substrate. LDL is one of the plasma lipoproteins whose oxidation is thought to contribute to the pathogenesis of atherosclerosis. The $Cu^{+2}$-promoted oxidation of LDL is a model for the free radical-induced oxidation of LDL that occurs in vivo.

The filter segment of a Marlboro Medium cigarette (Philip Morris Inc., Richmond, Va.) was treated with 5.0 $\mu$l of 2,6-diisopropylphenol (Aldrich Chemical Co., Milwaukee, Wis.) by the use of a fine-needle microsyringe. The cigarette (unlit) was attached to an adapter with a fine tube dipping into 0.50 mL of LDL (0.20 mg/mL) in phosphate-buffered saline (PBS). Reduced pressure exerted above the LDL solution resulted in air being drawn through the cigarette and then through the LDL solution in the form of fine bubbles. A total of 10 cc of air was drawn through at the rate of 1 cc/sec (Tube 1, described below). The process was repeated twice with two fresh tubes of LDL solution, with 20 cc of air (Tube 2) and 40 cc of air (Tube 3) drawn through the solution. The above process was further repeated in exactly the same way, but with untreated cigarettes (Tubes 4, 5, 6).

A solution of $CuSO_4$ (0.50 mM, 5.0 $\mu$l, final concentration 5.0 $\mu$M) was added to each tube to initiate the oxidation of LDL. The tubes were then capped and incubated at 37° C. for 6 hours. Next, the tubes were analyzed for the presence of lipid-derived oxidation products ("TBARS" or thiobarbituric acid reacting substances; principally, malondialdehyde) using standard methods known in the art. The pink color, resulting from the presence of TBARS, was measured spectrophotometrically at 532 nm.

Tubes 7-10 were also prepared and measured in parallel as controls. The following results were obtained:

|  |  | % OXIDATION |
| --- | --- | --- |
| Tube 1 | LDL solution, treated cigarette, 10 cc air, then $CuSO_4$ added | 19% |
| Tube 2 | LDL solution, treated cigarette, 20 cc air, then $CuSO_4$ added | 3% |
| Tube 3 | LDL solution, treated cigarette, 40 cc air, then $CuSO_4$ added | 0% |
| Tube 4 | LDL solution, untreated cigarette, 10 cc air, then $CuSO_4$ added | 94–100% |
| Tube 5 | LDL solution, untreated cigarette, 20 cc air, then $CuSO_4$ added | 94–100% |
| Tube 6 | LDL solution, untreated cigarette, 40 cc air, then $CuSO_4$ added | 94–100% |
| Tube 7 | LDL solution, no air bubbled through, no $CuSO_4$ added | 0% |
| Tube 8 | Same as 7, but $CuSO_4$ added | 95% |
| Tube 9 | Same as 7, but 0.50 $\mu$g of 2,6-diisopropylphenol added, then $CuSO_4$ added | 5% |
| Tube 10 | Same as 7, but 1.0 $\mu$g of 2,6-diisopropylphenol added, then $CuSO_4$ added | 2% |

The extent of oxidation was estimated by equating the absorbancy of tube 7 to 0% oxidation, and the absorbencies of tubes 4-6 to 100% oxidation. Separate experiments with higher concentrations of added copper confirmed that oxidation with 5.0 $\mu$M $CuSO_4$ was essentially complete.

These experiment demonstrate the efficacy of airborne 2,6-diisopropylphenol in inhibiting the $CuSO_4$ promoted oxidation of LDL. It may be roughly estimated, by comparing the results of Tubes 2, 9 and 10, that 10 cc of air delivered approximately 0.8 $\mu$g of 2,6-diisopropylphenol to the LDL solution.

EXAMPLE II

The experiment of Example 1 was repeated with several changes. The filter segments of four cigarettes were treated as follows:

| Cigarette 1: | Untreated (control) |
| --- | --- |
| Cigarette 2: | Treated with 5.0 mg of 2,6-diisopropylphenol in 50 $\mu$l of acetone, delivered with a fine-needle microsyringe. Sufficient air was then drawn through the cigarette to completely remove the solvent. |
| Cigarette 3: | Treated with 5.0 mg of 2,6-di-tert-butylphenol (Aldrich Chemical Co., St. Louis, MO) in the same manner as above. |
| Cigarette 4: | Treated with 5.0 mg of 2(3)-tert-butyl-4-methoxyphenol (BHA, Aldrich Chemical Co., St. Louis, MO) in the same manner as above. |

Air (20 cc) was drawn through each cigarette and then through 1.5 mL of LDL solution (0.20 mg/mL) in PBS. Aliquots of 0.50 mL of each solution were then treated with $CuSO_4$ to a final concentration of either 0.0 $\mu$M (control), 5.0 $\mu$M or 10.0 $\mu$M. After incubating the solutions at 37° C. for 6 hours, the solutions were analyzed for TBARS in the same manner as Example 1. The following results were obtained:

|  |  |  | % OXIDATION |
| --- | --- | --- | --- |
| Cigarette 1: | control (0% oxidation control) | 0 $\mu$M $CuSO_4$ | 0% |
| Cigarette 1: | control (100% oxidation control) | 5 $\mu$M $CuSO_4$ | 100% |
| Cigarette 1: | control (100% oxidation control) | 10 $\mu$M $CuSO_4$ | 100% |
| Cigarette 2: | (2,6-diisopropylphenol) | 5 $\mu$M $CuSO_4$ | 15% |
| Cigarette 2: | (2,6-diisopropylphenol) | 10 $\mu$M $CuSO_4$ | 100% |
| Cigarette 3: | (2,6-ditertbutylphenol) | 5 $\mu$M $CuSO_4$ | 10% |
| Cigarette 3: | (2,6-ditertbutylphenol) | 10 $\mu$M $CuSO_4$ | 10% |
| Cigarette 4: | (BHA) | 5 $\mu$M $CuSO_4$ | 15% |
| Cigarette 4: | (BHA) | 10 $\mu$M $CuSO_4$ | 100% |

These results demonstrate that the efficiencies of airborne delivery of protection against oxidation are similar for the three agents tested.

EXAMPLE III

Circles of filter paper (9 cm in diameter) were impregnated with 250 mg of the following agents:

| Filter paper 1: | No agent (untreated control) |
| --- | --- |
| Filter paper 2: | Probucol (Sigma Chemical Co., St. Louis, MO) (negative control) |
| Filter paper 3: | 2,6-di-tert-butyl-4-methylphenol (BHT) |
| Filter paper 4: | 2,6-diisopropylphenol |

The papers were placed separately in loosely covered translucent chambers of 4 liter capacity. Each chamber also contained a small tray with a thin layer (about 2 mm) of boiled linseed oil (Parks Corp., Somerset, Mass.), and a thin strip (about 4 mm) of freshly sliced lean beef. After 2 days at room temperature, which included 24 hours of incandescent illumination and 5 hours of bright sunshine, samples of the materials were analyzed.

Small samples of the beef were macerated in water at a concentration of 10 mg/mL. The hazy supernatants were analyzed for TBARS with the following results:

|  | RELATIVE TBARS COLOR |
| --- | --- |
| 1. Untreated control | 100 |
| 2. Probucol (negative control) | 100 |
| 3. BHT | 80 |
| 4. 2,6-diisopropylphenol | 25 |

The linseed oil samples showed physical differences. In chambers 1 and 2, the oil had a skin of polymer. In chamber 3, the oil was thickened but had no skin. In chamber 4, the oil was darker, but there was no polymer skin and the viscosity appeared to be unchanged. The TBARS assay of dispersions of the oil phases in 1:10 ethanol:water gave the following relative results:

|  | RELATIVE TBARS COLOR |
| --- | --- |
| 1. Untreated control | 100 |
| 2. Probucol (negative control) | 100 |
| 3. BHT | 90 |
| 4. 2,6-diisopropylphenol | 15 |

These results again demonstrate the efficacy of airborne 2,6-diisopropylphenol in protecting against free radical-induced oxidation processes. BHT also has some inhibiting effect, but the larger molecule probucol had no discernible effect.

The foregoing is offered primarily for purposes of illustration. It will be readily apparent to those skilled in the art that the operating conditions, materials, procedural steps and other parameters of the systems described herein may be further modified or substituted in various ways without departing from the spirit and scope of the present invention.

We claim:

1. A method for preventing oxidative damage to respiratory tissue, said method comprising exposing the tissue to a phenolic antioxidant compound in vapor form, said compound having the formula:

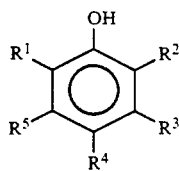

wherein $R^1$ and $R^2$ are independently selected from the group consisting of lower ($C_2$–$C_4$) alkyls, with the proviso that the total number of carbon atoms in $R^1$ and $R^2$ sum to at least 4;

$R^3$, $R^4$, and $R^5$ are members independently selected from the group consisting of H, lower ($C_1$–$C_6$) alkyls, lower ($C_1$–$C_4$) alkoxys, and lower alkyls in which one or more of the atoms is replaced by a heteroatom selected from the group consisting of O, N, and S, with the proviso that the total number of carbons and heteroatoms in groups $R^3$, $R^4$ and $R^5$ does not exceed 5; and wherein the antioxidant compound is a volatile substance incorporated into a tobacco smoking product.

2. The method according to claim 1, wherein said tobacco product contains a filter and said volatile antioxidant is incorporated into said filter, said method comprises smoking said tobacco product.

3. A method for preventing oxidative damage to biological tissue, the method comprising placing a tissue in a chamber filled with a phenolic antioxidant compound in vapor form, and exposing the tissue to the compound, said compound having the formula:

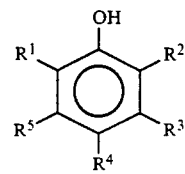

wherein $R^1$ and $R^2$ are independently selected from the group consisting of lower ($C_1$–$C_4$) alkyls, with the proviso that the total number of carbon atoms in $R^1$ and $R^2$ sum to at least 4; and $R^3$, $R^4$, and $R^5$ are members independently selected from the group consisting of H, lower ($C_1$–$C_6$) alkyls, lower ($C_1$–$C_4$) alkoxys, and lower alkyls in which one or more of the atoms is replaced by a heteroatom selected from the group consisting of O, N, and S, with the proviso that the total number of carbons and heteroatoms in groups $R^3$, $R^4$ and $R^5$ does not exceed 5.

4. A method for preventing oxidative damage to biological tissue, said method comprising exposing the tissue to a phenolic antioxidant compound in vapor form, said compound having the formula:

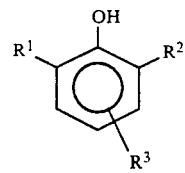

wherein $R^1$ and $R^2$ are members independently selected from the group consisting of tert-butyl and isopropyl groups; and $R^3$ is a member selected from the group consisting of H, lower ($C_1$–$C_6$) alkyls and lower ($C_1$–$C_4$) alkoxys.

5. The method according to claim 4, wherein said compound is 2,6-di-tert-butylphenol.

6. The method according to claim 4, wherein said compound is 2,6-di-tert-butyl-4-methylphenol.

7. The method according to claim 4, wherein said compound is 2,6-di-isopropylphenol.

* * * * *